United States Patent [19]

Maniar et al.

[11] Patent Number: 5,874,469
[45] Date of Patent: Feb. 23, 1999

[54] FLUOROALKYL HYDROCARBONS FOR ADMINISTERING WATER INSOLUBLE OR UNSTABLE DRUGS

[75] Inventors: Manoj L. Maniar, San Diego, Calif.; John C. Lang, Arlington, Tex.

[73] Assignee: Alcon Laboratories, Inc., Fort Worth, Tex.

[21] Appl. No.: 583,381

[22] Filed: Jan. 5, 1996

[51] Int. Cl.[6] .................. A61K 31/08; A61K 31/045; A61K 31/20; A61K 31/22
[52] U.S. Cl. .................. 514/550; 514/546; 514/557; 514/558; 514/675; 514/722; 514/724
[58] Field of Search .................. 514/550, 546, 514/557, 558, 675, 722, 724

[56] References Cited

U.S. PATENT DOCUMENTS

| | | | |
|---|---|---|---|
| 4,569,962 | 2/1986 | Burguette et al. | 522/74 |
| 4,990,283 | 2/1991 | Visca et al. | 252/309 |
| 5,118,494 | 6/1992 | Schultz et al. | 424/45 |
| 5,126,379 | 6/1992 | Volkert et al. | 521/110 |
| 5,137,650 | 8/1992 | Kaneko | 252/54 |
| 5,173,298 | 12/1992 | Meadows | 424/427 |
| 5,300,528 | 4/1994 | Graybill et al. | 514/772 |

FOREIGN PATENT DOCUMENTS

| | | |
|---|---|---|
| 0 112 658 A2 | 7/1984 | European Pat. Off. . |
| 0 136 102 A2 | 4/1985 | European Pat. Off. . |
| 0 089 815 B1 | 12/1986 | European Pat. Off. . |
| 0 091 313 B1 | 9/1990 | European Pat. Off. . |
| 53-78025720 | 7/1978 | Japan . |
| WO 91/14422 | 10/1991 | WIPO . |
| WO 92/05770 | 4/1992 | WIPO . |
| WO 93/18748 | 9/1993 | WIPO . |

OTHER PUBLICATIONS

Abougilale et al., "Perfluoroalkylated Fatty Acid Monoesters of Trehalose and Sucrose for Biomedical Applications: Remarkable Emulsifying Properties of 6–0–[3'–(Perfluorooctyl) propanoyl]–Trehalose," JAOCS, vol. 69, No. 1, 1992, p. 1–8.

Clark, Jr., et al., "Perfluorinated Organic Liquids and Emulsions as Biocompatible NMR Imaging Agents for 19F and Dissolved Oxygen," *Proceedings of the Meeting of the International Society on Oxygen Transport to Tissue* held Aug. 16–20, 1983 in Ruston, Louisiana, p. 835–845.

Ramharack, "Water–Borne Fluoropolymer Release Coatings for Adhesive Tapes 3. Fluorocarbon Release Systems," *J. of Water Borne Coatings*, 1986.

Rosen et al., "Fluorocarbon Emulsions," *Critical Care Medicine*, vol. 10, No. 3, 1982, p. 149–154.

Warren et al., Welsh School of Pharmacy, UWCC, Cardiff, UK;PDD 7100; "An Investigation of the Factors Influencing the Solubilization of Drugs Within Licithin Micelles in a Model CFC Solvent and a Commercial Propellant Blend," AAPS Meeting, 1993.

Zarif et al., "Biodistribution of Mixed Fluorocarbon–Hydrocarbon Dowel Molecules Used as Stabilizers of Fluorocarbon Emulsions: A Quantitative Study by Fluorine Nuclear Magnetic Resonance (NMR)," *Pharmaceutical Research*, vol. 11, No. 1, 1994, p. 122–127.

Zarif et al., "Synergistic Stabilization of Perfluorocarbon–Pluronic F–68 Emulsions by Perfluoroalkylated Polyhydroxylated Surfactants," *JAOCS*, vol. 66, No. 10, 1989, p. 1515–1523.

Zarif et al., J. Med. Chem., 33(4), 1262–1269, 1990.

*Primary Examiner*—Phyllis G. Spivak
*Attorney, Agent, or Firm*—Patrick M. Ryan

[57] ABSTRACT

Fluoroalkyl hydrocarbons as vehicles for pharmaceutical drugs are disclosed. These vehicles are particularly well-suited for delivering drugs which are insoluble in water or chemically unstable in aqueous media. Pharmaceutical solution compositions based on these vehicles have long shelf lives and provide improved drug bioavailability. In addition, the pharmaceutical compositions of the present invention are nonaqueous, and therefore do not require preservatives or tonicity agents. The invention is particularly useful in the field of ophthalmology.

16 Claims, No Drawings

FLUOROALKYL HYDROCARBONS FOR ADMINISTERING WATER INSOLUBLE OR UNSTABLE DRUGS

BACKGROUND OF INVENTION

The present invention relates to the field of ophthalmic drug formulation and delivery. More particularly, this invention relates to an improved method for formulating and administering pharmaceutical drugs which are insoluble or unstable in aqueous solutions.

Biologically active and/or diagnostic agents are conventionally formulated as solutions, suspensions, ointments, or gels (responsive or non-responsive to the ophthalmic environment); or are incorporated into (or absorbed onto) carriers such as solvated polymers, inclusion complexes, microspheres (monolithic or encapsulated), nanospheres, liposomes, ion exchange resins, or combinations of the above. These formulations typically contain water as one of the major components. Unfortunately, not all biologically active agents are chemically stable in an aqueous environment. Many classes of drugs include compounds which are therapeutically effective, but which are hydrolytically unstable. In particular, biologically active ergoline derivatives, such as cabergoline, are highly unstable when placed in an aqueous environment. More generally, prodrugs and soft drugs, which are becoming increasingly important due to improved delivery and targeting, are often subject to hydrolytic degradation, especially on prolonged storage in aqueous environments. In view of the relative instability of such compounds, it is not possible to incorporate these compounds in aqueous solutions, or other types of aqueous compositions which may be stored for relatively long periods (i.e., several months or more) prior to use.

Compounds which are insoluble in water are frequently soluble in hydrocarbon or silicone oils, triglycerides (such as the medium-chain triglycerides commercially available as Miglyols®), waxes, etc. or in stabilized emulsions (utilizing lipids or surfactants) of these solvents. However, formulations which utilize oils as the vehicle for the active drug are not ideal. This is particularly true with respect to ophthalmic compositions. Among other disadvantages, oils may obscure vision of patients, thereby adversely affecting patient compliance, and high oil/water partition coefficients of compounds may reduce bioavailability.

Various solutions to the above-cited problem have been proposed. One approach has been to use perfluorocarbons as vehicles for delivering drugs to the skin or eyes.

EP-A-0 091 313 describes the use of perfluorocarbons as vehicles for delivering drugs. The perfluorocarbons are utilized in the form of solutions or suspensions. Unfortunately, it has been found that many drugs will not dissolve in perfluorocarbons. It is therefore not possible to form perfluorocarbon solutions containing these compounds.

WO 92/05770 and WO 93/18748 disclose compositions comprising drug carriers (referred to as "drug delivery vehicles" in the references) suspended in nonaqueous liquid vehicles (referred to as "carriers" in the references). The nonaqueous liquid vehicles are perfluorocarbons or fluorinated silicones. The perfluorocarbons useful in the reference compositions include perfluorocyclocarbons, acyclic perfluorocarbons and their derivatives. These references also disclose that the perfluorocarbon derivatives are typically nitrogen and oxygen containing compounds such as amines and ethers. The nonaqueous liquid vehicles, however, are preferably perfluorinated, meaning that all of the hydrogens bonded to carbons of the vehicle compounds are substituted with fluorine.

Solutions are generally preferable to suspensions for drug delivery. This is particularly true in the field of ophthalmic drug delivery. Thus, there is need for improved solution vehicles to deliver drugs which are unstable or insoluble in aqueous media.

Accordingly, it is a principal object of the present invention to provide pharmaceutical solutions for delivering water-labile, biologically active drugs through a wide variety of acceptable routes of drug administration. It is a further object of the present invention to provide pharmaceutical compositions containing biologically active drugs which exhibit improved shelf life and stability.

It is an additional object of the present invention to provide pharmaceutical compositions which release the dissolved drug effectively at the desired site of action.

A further object of the present invention is to provide ophthalmic compositions which are comfortable, non-toxic, transparent, non-irritating, odorless, and do not cause blurring of vision when administered to the eye.

SUMMARY OF THE INVENTION

The present invention accomplishes the foregoing objectives by utilizing fluoroalkyl hydrocarbons, or mixtures of fluoroalkyl hydrocarbons and perfluorocarbons, as vehicles for pharmaceutical drugs which are insoluble and/or unstable in aqueous media. The pharmaceutical compositions of the present invention are solutions and are very stable over extended periods of storage. The compositions are particularly well suited for use in connection with the diagnosis or treatment of injuries or diseases of the eye. However, those skilled in the art will appreciate that the pharmaceutical compositions of the present invention are equally well suited for use in applications to other physiological environments where repeated administration of a drug delivery vehicle to sensitive tissue areas is required.

DESCRIPTION OF PREFERRED EMBODIMENTS

As utilized herein, the term "perfluorocarbon" means a cyclic or acyclic, branched or non-branched, organic compound, in which all or substantially all hydrogen atoms attached to carbon atoms are replaced by fluorine, and the term "substituted derivatives thereof" in relation to perfluorocarbons means perfluorocarbons wherein one or more carbon atoms have been replaced or substituted with heteroatoms (such as oxygen, nitrogen, sulfur or silicon) or halogen atoms. Included within the scope of substituted derivatives of perfluorocarbons are perfluorocarbons containing ether, ester, carbonate, urethane, ketone or aldehyde groups.

The compounds utilized as drug solubilizers and vehicles in the present invention are referred to herein as "fluoroalkyl hydrocarbons". As utilized herein, the term "fluoroalkyl hydrocarbon" means a liquid compound which includes two cyclic or acyclic (branched or unbranched) groups, wherein one group is a fluorophilic moiety and the other is a fluorophobic moiety. The fluorophilic moiety is (referred to below as the "A" group) is a perfluorocarbon or substituted derivative thereof. The fluorophobic moiety (referred to below as the "B" group) is a chemically stable organic group containing at least one oxygen atom, wherein any carbon valence in the B group may be completed with hydrogen, fluorine, or heteroatoms, provided that B is not predominately fluorinated.

If the fluorophilic moiety were separated from the fluorophobic moiety and terminated with fluorine, the fluorophilic moiety would be soluble in perfluorocarbons. Likewise, if the fluorophobic moiety were separated from the fluorophilic moiety and terminated with hydrogen, the fluorophobic moiety would be soluble in a hydrocarbon or substituted hydrocarbon.

The fluorophobic moiety provides the solubilizing power to dissolve a drug at desired herapeutic concentrations. The selection of functionalities for the fluorophobic moiety is dependent upon the characteristics and/or structure of the chosen therapeutic agent. The selection of the fluorophilic moiety is dependent upon whether the fluoroalkyl hydrocarbon will be chosen as the solvent for the drug or whether the fluoroalkyl hydrocarbon will function as a solubilizer for the drug in a perfluorocarbon solvent.

The fluoroalkyl hydrocarbons which may be utilized in the present invention include compounds having the following structure:

A–B where A and B are defined as follows:
  A is a perfluorocarbon or substituted derivative thereof; and
  B is a chemically stable organic group containing at least one oxygen atom, wherein any carbon valence in the B group may be completed with hydrogen, fluorine, or heteroatoms, provided that B is not predominantly fluorinated.

Suitable B groups include linear or cyclic, branched or unbranched, substantially hydrogenated hydrocarbons, optionally substituted with halogen atoms, heteroatoms or finctional groups, such as an alcohol, acid, ether, ester, carbonyl, carbonate, urethane, ketone or aldehyde group. The B group preferably contains no more than one fluorine atom.

The following compounds are representative examples of the above-described fluoroalkyl hydrocarbons:

| Chemical Structure | Name |
|---|---|
| 1. F(CF$_2$)$_6$CH$_2$CH$_2$OH<br>where A = F(CF$_2$)$_6$–<br>and B = –CH$_2$CH$_2$OH. | 1H,1H,2H,2H-Perfluorooctanol |
| 2. F(CF$_2$)$_7$COOH<br>where A = F(CF$_2$)$_7$–<br>and B = –COOH. | Perfluoro-n-octanoic acid |
| 3. F(CF$_2$)$_8$CH$_2$CH$_2$OH<br>where A = F(CF$_2$)$_8$–<br>and B = –CH$_2$CH$_2$OH. | 1H,1H,2H,2H-Perfluorodecanol |
| 4. CF$_3$CF$_2$CF$_2$OCF(CF$_3$)COOH<br>where A = CF$_3$CF$_2$CF$_2$OCF(CF$_3$)–<br>and B = –COOH. | Dodecafluoro-2-methyl-3-oxa-hexanoic acid |
| 5. CF$_3$CF$_2$CH$_2$OH<br>where A = CF$_3$CF$_2$–<br>and B = –CH$_2$OH. | 1H,1H-Pentafluoropropanol-1 |
| 6. HF$_2$CCF$_2$OC$_4$H$_9$<br>where A = HF$_2$CCF$_2$–<br>and B = –OC$_4$H$_9$. | n-Butyl-1,1,2,2-tetrafluoro-ethyl ether |
| 7. F$_3$C(CH$_3$)CHOOCCH$_3$<br>where A = F$_3$C–<br>and B = –CHOOCCH$_3$. | 1,1,1-trifluoroisopropyl acetate |
| 8. F$_3$CCH$_2$OOCCH$_3$<br>where A = F$_3$C–<br>and B = –CH$_2$OOCCH$_3$. | 2,2,2-trifluoroethyl acetate |
| 9. F$_3$CCOCH$_2$COC(CH$_3$)$_3$<br>where A = F$_3$C–<br>and B = –COCH$_2$COC(CH$_3$)$_3$. | 1,1,1-Trifluoro-5,5-dimethyl-2,4-hexanedione |
| 10. F[CF(CF$_3$)CF$_2$O]$_2$CF(CF$_3$)COOCH$_3$<br>where<br>A = F[CF(CF$_3$)CF$_2$O]$_2$CF(CF$_3$)– | Perfluoro-2,5-dimethyl-3,6-dioxanonanoic acid, methyl ester (C$_{10}$H$_3$F$_{17}$O$_4$) |
| 11. CF$_3$CF$_2$CF$_2$OCF(CF$_3$)COOCH$_3$<br>where A = CF$_3$CF$_2$CF$_2$OCF(CF$_3$)–<br>and B = –COOCH$_3$. | Methyl undeca-fluoro-2-methyl-3-oxa-hexanoate |
| 12. (CF$_3$)$_2$CHOH<br>where A = (CF$_3$)– and B = –CHOH, and the branched compound can be represented as A$_2$B. | Hexafluoroisopropanol |

The compounds of formula (I) and formula (II) below are particularly preferred:

$$F(CF_2)_n CH_2 CH_2 OH \qquad (I)$$

wherein n is 1 to 16; and $$F(CF_2)_n-O-\underset{\underset{F}{|}}{\overset{\overset{CF_3}{|}}{C}}-COOCH_3 \qquad (II)$$

wherein n is 3 to 16. In formula (I), A=F(CF$_2$)$_n$— and B=—CH$_2$CH$_2$OH. In formula (II), A=F(CF$_2$)$_n$OC(CF$_3$)F— and B=—COOCH$_3$.

The most preferred compounds are: compound #1 above; compound #11 above; and mixtures of these compounds. All of the above-described compounds are commercially available. For example, the compounds may be obtained from Peninsular Chem Research ("PCR"), P.O. Box 1466, Gainesville, Fla. 32602.

The fluoroalkyl hydrocarbons utilized in the present invention must either be soluble in perfluorocarbon or be liquid at room temperature. The delivery vehicle will preferably be a liquid at room temperature, but may contain hydrofluorocarbon polymers to increase viscosity or elasticity (e.g., Galden HT90 and HT 110, available from Aussimont USA). These compounds are miscible with each other or dissolve in one another. However, none of the above compounds will be substantially soluble in water.

The fluoroalkyl hydrocarbon vehicles of the present invention have several advantages. For example, pharmaceutical compositions based on these vehicles do not require any preservatives to maintain sterility, since the vehicles are non-aqueous. Thus, it is possible to package the compositions in a multi-dose container. Also, because the compositions are nonaqueous, neither pH nor tonicity need be considered in avoiding irritation and stinging upon instillation in the eye.

As explained above, the fluoroalkyl hydrocarbon vehicles of the present invention are particularly well-suited for delivering drugs that are insoluble or unstable in aqueous media. As utilized herein, the term "substantially insoluble" means that the drug is either totally insoluble in water or is so poorly soluble that formulating an aqueous pharmaceutical composition containing the drug is practically impossible or undesirable. Many drugs fall into at least one of these two categories. Classes of drugs which are known to be relatively unstable and/or insoluble in aqueous vehicles include: antiglaucoma drugs (e.g., α-, and β-adrenergic agonists and antagonists, dopaminergic agonists and antagonists, muscarinics and cholinergics); antibiotics (e.g., lactarn antibiotics); steroids; antioxidants; antiproliferative agents; immunosuppressants; retinoids (e.g., tretinoin and other retinoic acid derivatives); non-steroidal antiinflammatory drugs ("NSAIDs"); aldose reductase inhibitors; ergoline derivatives (e.g., cabergoline); and various other classes of drugs known to those skilled in the art. The vehicles are especially suitable for delivering prodrugs, soft drugs, co-drugs and drug conjugates, all of which are subject to hydrolysis. Finally, proteins and oligonucleotides (e.g., utilized in anti-sense and triplex genetic therapies) are notoriously unstable for long-term storage in aqueous solutions. These classes of materials would benefit significantly from the delivery/formulation technology disclosed herein. Further examples of specific drugs from the above-cited classes are presented below:

Antibiotics
   Cephaloridine
   Cefamandole
   Cefamandole nafate
   Cefazolin
   Cefoxitin
   Cephacetrile sodium
   Cephalexin
   Cephaloglycin
   Cephalosporin C
   Cephalothin
   Nafcillin
   Cephamycins
   Cephapirin sodium
   Cephradine
   Penicillin BT
   Penicillin N
   Penicillin O
   Phenethicillin potassium
   Pivampic ulin
   Amoxicillin
   Ampicillin
   Cefatoxin
   Cefotaxime
   Moxalactam
   Cefoperazone
   Cefsulodin
   Ceflizoxime
   Ceforanide
   Cefiaxone
   Ceftazidime
   Thienamycin
   N-Formimidoyl thienamycin
   Clavulanic acid
   Penemcarboxylic acid
   Piperacillin
   Sulbactam
Steroids
   Prednisolone
   Prednisolone acetate
   Hydrocortisone
   Hydrocortisone acetate
   Hydrocortisone valerate
   Vidarabine
   Fluorometholone
   Fluocinolone acetonide
   Triamcinolone acetonide
   Dexamethasone
   Dexamethasone acetate
Non-Steroidal Antiinflammatories
   Indomethacin
   Bromfenac
   Ibuprofen
   Diclofenac
   oxyphenbutazone
   Suprofen
   Ketorolac
   Bromfenac
   Diclofenac
   Suprofen
Retinoids
   All-trans-retinoic acid (Tretinoin)
   13-cis-retinoic acid (Isotretinoin)

Although the fluoroalkyl hydrocarbon vehicles of the present invention are particularly useful for delivering drugs which are unstable or insoluble in aqueous media, these compounds are also useful for delivering a variety of other drugs because of the inherent advantages of these vehicles. For example, the high density and low viscosity of the vehicle allows a small drop volume to be utilized for administration of ophthalmic drugs. As a result, there is less spillage of the instilled dose from the eye and bioavailability of the drug is increased. Additionally, the drainage rate of the instilled dose from the eye is reduced due to diminished excess tear volume.

The following representative examples are presented to illustrate further the pharmaceutical compositions and drug delivery methods of the present invention. The compositions described below are particularly well-suited for treating ocular injuries and diseases. However, it should be emphasized that the pharmaceutical compositions of the present invention may be utilized through all common routes of administration, such as oral, dermal, intravenous, nasal and others known in the art.

EXAMPLE 1

0.00471 grams ("g") of cabergoline was added to 1 milliter ("mL") of perfluorooctanol (PFO). The suspension was sonicated for 15 minutes and then filtered through a 0.45µ filter. 100 microliters ("µL") of the filtrate was extracted with 1 mL of phosphate buffer (pH 3.0). 10 µL of the aqueous portion was analyzed for cabergoline by injecting in onto the HPLC. The mobile phase was made as follows:

5.2 mL of concentrated phosphoric acid, 6.0 mL of tetrabutyl ammonium hydroxide, and 6.612 g of dibasic ammonium phosphate were added to 1500 mL of deionized water. The mixture was stirred until it formed a clear solution. To the above solution 1800 mL of acetonitrile, 400 mL of tetrahydrofuran and sufficient water were added to make 4 liters of mobile phase. The mobile phase was pumped at 1.5 mL/minute through a cyano column. The eluent was monitored at 280 nanometers ("nm"). HPLC analysis showed that the solubility of cabergoline in perfluorooctanol was 2700 ppm.

EXAMPLE 2

0.00126 g of cabergoline was added to 1 mL of perfluoro-2-methyl-oxahexanoic acid, methyl ester ("12205-1"). The suspension was sonicated for 15 minutes and then filtered through a 0.45µ filter. 100 µL of the filtrate was extracted with 1 mL of phosphate buffer (pH 3.0). 10 µL of the aqueous portion was analyzed for cabergoline by injecting it onto the HPLC. The procedure used for analysis was the same as in Example 1 above. The solubility of cabergoline in 12205-1 was found to be 1035 ppm. Thus, one can obtain a range of solubility of cabergoline using different ratios of PFO and 12205-1.

EXAMPLE 3

0.0056 g of cabergoline was weighed in a vial. 5 mL of perfluoro-2-methyl-oxahexanoic acid, methyl ester (i.e., PCR compound number 12205-1) was added by a volumetric pipette. The mixture was vortexed well and then sonicated for 30 minutes. The suspension was filtered through a 0.2μ acrodisc. The filtrate was split into 3 vials. The vials were stored at room temperature ("RT"), 40° C. and 50° C. The vial stored at room temperature was wrapped in aluminum foil. 100 μL of sample was withdrawn as a function of time. 1 mL of pH 3.0 phosphate buffer was added to the sample and vortexed. The supernatant was taken and analyzed by HPLC as described above. The results are shown in FIG. 1b. FIG. 1b indicates that there is no hydrolysis of cabergoline and thus is expected to be stable during the shelf life.

EXAMPLE 4

0.01847 g of leflunomide was added to 1 mL of perfluorooctanol ("PFO"). The suspension was sonicated for 15 minutes. The suspension was filtered through a 0.45μ filter and 100 μL of the filtrate was extracted with 1 mL of the mobile phase for leflunomide. The mobile phase consisted of 40:60 of acetonitrile: 0.01m $NaH_2PO_4$ adjusted to pH 7.0. 10 μL of the extract was injected on to a C-18 reverse phase column. The sample was eluted with the mobile phase with a flow rate of 2 mL/minute and monitored at 254 nm. The solubility of leflunomide in perfluorooctanol was found to be 2000 ppm.

EXAMPLE 5

0.00207 g of leflunomide was added to 1 mL of perfluoro-2-methyl-oxahexanoic acid, methyl ester (12205-1). The suspension was filtered through a 0.45μ filter and 100 μL of the filtrate was extracted with 1 mL of the mobile phase of leflunomide. 10 μL of the extract was injected on to HPLC to determine the solubility of leflunomide. The solubility of leflunomide in 12205-1 was found to be 238 ppm. Thus, one can obtain a range of solubility of leflunomide using different ratios of PFO and 12205-1.

EXAMPLE 6

0.0037 g of leflunomide ("AL2806") was added to 7 mL of perfluoro-2-methyl-oxahexanoic acid, methyl ester (12205-1) and sonicated for 30 minutes. The suspension was filtered and the filtrate was put on stability testing at 60° C. in an oven. 100 μL of sample was withdrawn as a function of time. The vehicle was evaporated and the residual sample was reconstituted in 1 mL of the mobile phase for leflunomide. The sample was analyzed by HPLC to determine the leflunomide content. The results are shown in FIG. 2b. As shown in FIG. 2b, there was no hydrolysis of leflunomide. The composition is therefore expected to be stable during storage.

EXAMPLE 7

0.00445 g of betaxolol was added to a 2 mL volumetric flask. About 1 mL of perfluoro-2-methyl-oxahexanoic acid, methyl ester (12205-1) was added to the flask and vortexed for a few minutes. To the suspension was added 0.00215 g of dipivefrin, and enough vehicle was added to bring the volume to 2 mL. The suspension was sonicated and then filtered. 100 μL of the filtrate was extracted with 1 mL of pH 3.0 phosphate buffer. The aqueous portion of the extract was analyzed by reverse phase HPLC using a C 18 column and the mobile phase consisting of acetonitrile/sodium phosphate buffer, pH 3.0/dimethyl amine. The solubility of each drug in perfluoro-2-methyl-oxahexanoic acid, methyl ester was found to be greater than 1000 ppm.

EXAMPLE 8

Excess dipivefrin was stirred with perfluoro-2-methyl-oxahexanoic acid, methyl ester (12205-1) for 30 minutes. The solution was filtered through a 0.2μ filter and 100 μl of the sample was extracted with phosphate buffer (pH 3.0). The aqueous portion was analyzed for dipivefrin. The solubility of dipivefrin in 12205-1 was found to be greater than 1000 ppm.

What is claimed is:

1. A pharmaceutical solution composition which comprises a therapeutically effective amount of a drug and a non-aqueous liquid vehicle for the drug, said vehicle comprising a fluoroalkyl hydrocarbon selected from the group consisting of:

$F(CF_2)_nCH_2CH_2OH$ wherein n is 1 to 16;

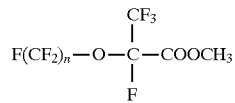

wherein n is 3 to 16;

$F(CF_2)_7COOH$;

$CF_3CF_2CF_2OCF(CF_3)COOH$;

$CF_3CF_2CH_2OH$;

$HF_2CCF_2OC_4H_9$;

$F_3C(CH_3)CHOOCCH_3$;

$F_3CCH_2OOCCH_3$;

$F_3CCOCH_2COC(CH_3)_3$;

$F[CF(CF_3)CF_2O]_2CF(CF_3)COOCH_3$; and $(CF_3)_2CHOH$.

2. A phannaceutical composition according to claim 1, wherein the fluoroalkyl hydrocarbon is selected from the group consisting of n-butyl-1,1,2,2-tetrafluoroethyl ether; 1,1,1-trifluoroisopropyl acetate; 2,2,2-trifluoroethyl acetate; 1,1,1-trifluoro-5,5-dimethyl-2,4-hexanedione; 1H,1H,2H,2H-perfluorooctanol; perfluoro-n-octanoic acid; perfluoro-2,5-dimethyl-3,6-dioxanonanoic acid, methyl ester; 1H,1H,2H,2H-perfluorodecanol; methyl undecafluoro-2-methyl-3-oxahexanoate; hexafluoroisopropanol; dodecafluoro-2-methyl-3-oxahexanoic acid; and 1H,1H-pentafluoropropanol-1.

3. A pharmaceutical solution composition according to claim 2, wherein the fluoroalkyl hydrocarbon comprises methyl undecafluoro-2-methyl-3-oxahexanoate.

4. A pharmaceutical solution composition according to claim 2, wherein the fluoroalkyl hydrocarbon comprises 1H,1H,2H,2H-perfluorooctanol.

5. A pharmaceutical solution composition according to claim 2, wherein the fluoroalkyl hydrocarbon comprises a mixture of methyl undecafluoro-2-methyl-3-oxahexanoate and 1H,1H,2H,2H-perfluorooctanol.

6. A pharmaceutical solution composition according to claim 1, wherein the fluoroalkyl hydrocarbon has the formula:

$$F(CF_2)_nCH_2CH_2OH$$

wherein n is 1 to 16.

7. A pharmaceutical solution composition according to claim 1, wherein the fluoroalkyl hydrocarbon has the formula:

$$F(CF_2)_n\text{---}O\text{---}\underset{\underset{F}{|}}{\overset{\overset{CF_3}{|}}{C}}\text{---}COOCH_3$$

wherein n is 3 to 16.

8. A pharmaceutical solution composition according to claim 1, wherein the drug is hydrolytically unstable.

9. A pharmaceutical solution composition according to claim 1, wherein the drug is substantially insoluble in water.

10. A method of formulating a pharmaceutical solution composition containing a drug which is unstable or substantially insoluble in water, which comprises dissolving the drug in a fluoroalkyl hydrocarbon, whereby the drug is uniformly dispersed in the composition and is chemically stable, wherein the composition is a non-aqueous composition and the fluoroalkyl hydrocarbon is selected from the group consisting of:

$$F(CF_2)_nCH_2CH_2OH$$
wherein n is 1 to 16;

$$F(CF_2)_n\text{---}O\text{---}\underset{\underset{F}{|}}{\overset{\overset{CF_3}{|}}{C}}\text{---}COOCH_3$$

Wherein n is 3 to 16;
$F(CF_2)_7COOH$;
$CF_3CF_2CF_2OCF(CF_3)COOH$;
$CF_3CF_2CH_2OH$;
$HF_2CCF_2OC_4H_9$;
$F_3(CH_3)CHOOCCH_3$;
$F_3CCH_2OOCCH_3$;
$F_3CCOCH_2COC(CH_3)_3$;
$F[CF(CF_3)CF_2O]_2CF(CF_3COOCH_3$; and
$(CF_3)_2CHOH$.

11. A method according to claim 10, wherein the fluoroalkyl hydrocarbon is selected from the group consisting of n-butyl-1,1,2,2-tetrafluoroethyl ether; 1,1,1-trifluoroisopropyl acetate; 2,2,2-trifluoroethyl acetate; 1,1,1-trifluoro-5,5-dimethyl-2,4-hexanedione; 1H,1H,2H,2H-perfluorooctanol; perfluoro-n-octanoic acid; perfluoro-2,5-dimethyl-3,6-dioxanonanoic acid methyl ester; 1H,1H,2H,2H-perfluorodecanol; methyl undecafluoro-2-methyl-3-oxahexanoate; hexafluoroisopropanol; dodecafluoro-2-methyl-3-oxahexanoic acid; and 1H,1H-pentafluoropropanol-1.

12. A method according to claim 11, wherein the fluoroalkyl hydrocarbon comprises methyl undecafluoro-2-methyl-3-oxahexanoate.

13. A method according to claim 11, wherein the fluoroalkyl hydrocarbon comprises 1H,1H,2H,2H-perfluorooctanol.

14. A method according to claim 11, wherein the fluoroalkyl hydrocarbon comprises a mixture of methyl undecafluoro-2-methyl-3-oxahexanoate and 1H,1H,2H,2H-perfluorooctanol.

15. A method according to claim 10, wherein the fluoroalkyl hydrocarbon has the formula:

$$F(CF_2)_nCH_2CH_2OH$$

wherein n is 1 to 16.

16. A method according to claim 10, wherein the fluoroalkyl hydrocarbon has the formula:

$$F(CF_2)_n\text{---}O\text{---}\underset{\underset{F}{|}}{\overset{\overset{CF_3}{|}}{C}}\text{---}COOCH_3$$

wherein n is 3 to 16.

* * * * *